US010456056B2

(12) United States Patent
Govari et al.

(10) Patent No.: US 10,456,056 B2
(45) Date of Patent: Oct. 29, 2019

(54) COMBINATION TORSO VEST TO MAP CARDIAC ELECTROPHYSIOLOGY

(71) Applicant: Biosense Webster (Israel) Ltd., Yokneam (IL)

(72) Inventors: Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 56 days.

(21) Appl. No.: 15/629,197

(22) Filed: Jun. 21, 2017

(65) Prior Publication Data
US 2018/0368716 A1    Dec. 27, 2018

(51) Int. Cl.
| A61B 5/0402 | (2006.01) |
|---|---|
| A61B 5/042 | (2006.01) |
| A61B 5/00 | (2006.01) |
| A61B 5/0408 | (2006.01) |
| A61B 5/053 | (2006.01) |

(52) U.S. Cl.
CPC .......... *A61B 5/0422* (2013.01); *A61B 5/0402* (2013.01); *A61B 5/6805* (2013.01); *A61B 5/04085* (2013.01); *A61B 5/0538* (2013.01)

(58) Field of Classification Search
None
See application file for complete search history.

(56) References Cited

U.S. PATENT DOCUMENTS

| 3,409,007 A | 11/1968 | Fuller |
|---|---|---|
| 3,610,250 A | 10/1971 | Sarbacher |
| 4,583,547 A | 4/1986 | Granek |
| 4,763,660 A | 8/1988 | Kroll |
| 5,184,620 A | 2/1993 | Cudahy |
| 5,443,489 A | 8/1995 | Ben-Haim |
| 5,480,422 A | 1/1996 | Ben-Haim |

(Continued)

FOREIGN PATENT DOCUMENTS

| GB | 2510452 A | 8/2014 |
|---|---|---|
| WO | 95/02995 A1 | 2/1995 |

(Continued)

OTHER PUBLICATIONS

Extended European search report for corresponding European patent application No. EP 18178720.1, dated Oct. 25, 2018.

*Primary Examiner* — Kennedy Schaetzle
(74) *Attorney, Agent, or Firm* — Notaro, Michalos & Zaccaria P.C.

(57) ABSTRACT

Cardiac catheterization is carried out by clothing a subject in a torso vest having a plurality of sensing electrodes, magnetic location sensors, active current location sensors and patches for establishing galvanic contact with the skin. A multi-electrode probe is inserted into a cardiac chamber such that a plurality of intracardiac electrodes are disposed at respective locations in the heart. Respective locations are determined using the active current location sensors, Electrical calibration signals are emitted from the intracardiac electrodes, and received in the sensing electrodes of the torso vest. Relationships between the emitted calibration signals and the received calibration signals in the intracardiac electrodes are established to map a correspondence between the received calibration signals and the respective locations.

11 Claims, 6 Drawing Sheets

(56) References Cited

U.S. PATENT DOCUMENTS

| | | | |
|---|---|---|---|
| 5,546,951 | A | 8/1996 | Ben-Haim |
| 5,558,091 | A | 9/1996 | Acker et al. |
| 5,568,809 | A | 10/1996 | Ben-Haim |
| 6,147,480 | A | 11/2000 | Osadchy et al. |
| 6,373,240 | B1 | 4/2002 | Govari |
| 6,584,343 | B1 | 6/2003 | Ransbury |
| 6,690,963 | B2 | 2/2004 | Ben-Haim et al. |
| 6,995,729 | B2 | 2/2006 | Govari et al. |
| 6,997,924 | B2 | 2/2006 | Schwartz et al. |
| 7,072,721 | B1 | 7/2006 | Trent |
| 7,321,228 | B2 | 1/2008 | Govari |
| 7,397,364 | B2 | 7/2008 | Govari |
| 7,729,742 | B2 | 6/2010 | Govari |
| 7,957,784 | B2 | 6/2011 | Voth |
| 7,974,680 | B2 | 7/2011 | Govari |
| 7,983,743 | B2 | 7/2011 | Rudy et al. |
| 8,019,402 | B1 | 9/2011 | Kryzpow |
| 8,046,050 | B2 | 10/2011 | Govari et al. |
| 8,433,387 | B2 | 4/2013 | Voth |
| 8,529,461 | B2 | 9/2013 | Revishvili |
| 8,818,482 | B2 | 8/2014 | Phillips |
| 8,897,851 | B2 | 11/2014 | Caprio |
| 9,024,619 | B2 | 5/2015 | Caprio |
| 9,320,446 | B2 | 4/2016 | Gillberg |
| 9,370,312 | B2 | 6/2016 | Schwartz |
| 2001/0039413 | A1* | 11/2001 | Bowe ............... A61M 25/0041 604/532 |
| 2003/0120150 | A1 | 6/2003 | Govari |
| 2003/0120163 | A1 | 6/2003 | Rudy |
| 2004/0068178 | A1 | 4/2004 | Govari |
| 2006/0173251 | A1 | 8/2006 | Govari et al. |
| 2007/0038078 | A1 | 2/2007 | Osadchy |
| 2008/0058657 | A1 | 3/2008 | Schwartz et al. |
| 2008/0161669 | A1 | 7/2008 | Hauck et al. |
| 2008/0294258 | A1 | 11/2008 | Revie |
| 2009/0088633 | A1 | 4/2009 | Meyer |
| 2012/0330179 | A1 | 12/2012 | Yuk |
| 2013/0018251 | A1 | 1/2013 | Caprio |
| 2014/0221803 | A1 | 8/2014 | Bar-Tal et al. |
| 2014/0323882 | A1 | 10/2014 | Ghosh |
| 2015/0133759 | A1 | 5/2015 | Govari |
| 2015/0157231 | A1 | 6/2015 | Gillberg |
| 2015/0265840 | A1 | 9/2015 | Ghosh |
| 2015/0320515 | A1 | 11/2015 | Edwards et al. |
| 2017/0135633 | A1* | 5/2017 | Connor ............... A61B 5/4866 |
| 2018/0137687 | A1 | 5/2018 | Katz et al. |

FOREIGN PATENT DOCUMENTS

| | | |
|---|---|---|
| WO | 96/05768 A1 | 2/1996 |
| WO | 97/24983 A2 | 7/1997 |
| WO | 98/29033 A1 | 7/1998 |
| WO | 99/05962 | 2/1999 |

\* cited by examiner

COMBINATION TORSO VEST TO MAP CARDIAC ELECTROPHYSIOLOGY

COPYRIGHT NOTICE a portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for performing medical examinations of the interior of the body. More particularly, this invention relates to improvements in electrical mapping of the heart using garments specially adapted to be worn on the surface of the body.

2. Description of the Related Art

The meanings of certain acronyms and abbreviations used herein are given in Table 1.

TABLE 1

Acronyms and Abbreviations

| | |
|---|---|
| ECG | Electrocardiogram |
| ACL | Active Current Location |

Methods are known for noninvasive mapping of electrical potentials in the heart based on body surface electrocardiographic (ECG) techniques. These methods combine 3-dimensional imaging with the ECG data in order to generate 3-dimensional maps of the electrical potentials on the epicardial surface, and on the endocardial surface, as well.

U.S. Pat. No. 7,983,743 to Rudy et al., which is herein incorporated by reference, proposes noninvasive systems and methods for determining electrical activity for a heart of a living being. A processor is configured to meshlessly compute data that represents heart electrical activity from a set of noninvasively measured body surface electrical potentials. This is accomplished using data that describes a geometric relationship between a plurality of locations corresponding to where the body surface electrical potentials were measured and the heart.

Reverse ECG mapping as, described in U.S. Pat. No. 7,983,743 attempts to generate an intracardiac ECG map by measuring body surface potentials at an array of positions on the skin of a patient. The method assumes that intracardiac ECG potentials $\vec{E}$ generate body surface potentials $\vec{S}$ and that the two sets of potentials are related by an equation of the form:

$$\vec{S} = M \cdot \vec{E} \qquad (1),$$

where M is a matrix, having elements $m_{ij}$.

The values of elements of the matrix M depend, inter alia, on the distance between the positions on the heart surface and the positions on the patient's skin, and on the conductivity of the material between these positions.

Commonly assigned U.S. Patent Application Publication No. 2008/0058657 by Schwartz et al., which is herein incorporated by reference, describes construction of a matrix relationship between a small number of endocardial points and a large number of external receiving points using a multi-electrode chest panel. Inversion of the matrix yields information allowing the endocardial map to be constructed.

Commonly assigned U.S. Patent Application Publication No. 2015/0133759 by Govari et al., which is herein incorporated by reference, describes a technique of injecting signals from an array of vest electrodes, and detecting them in a catheter positioned within the heart. A matrix is generated, inverted, and multiplied by subsequent vest electrode potentials to get heart potentials.

SUMMARY OF THE INVENTION according to disclosed embodiments of the invention, a vest having an array of electrodes is used in a manner, which is essentially the inverse of the technique described in the above-noted U.S. Patent Application Publication No. 2015/0133759. Signals are emitted by a catheter at a known position in the heart and received in the vest array. A matrix describing correspondence between signals emitted at the catheter locations and received in a vest array is established. The catheter can then be withdrawn. Thereafter, intrinsic cardiac bioelectric signals originating at the known locations can be evaluated noninvasively by exploitation of the matrix and analysis of time-varying readings from the vest array.

Conventionally, in order to perform procedures such as described in the above-noted U.S. Patent Application Publication No. 2015/0133759, different types of electrodes are attached to the skin of the patient. These may include electrocardiogram (ECG) electrodes, active current location (ACL) electrodes for measuring impedance, an ablation "indifferent" electrode for ablation current return, a reference electrode for unipolar pacing, and defibrillation patches. Apart from these electrodes, other elements such as location sensors may need to be attached to, or positioned close to, the patient. Placing all the electrodes and other elements separately on the patient is cumbersome, tedious, and prolongs the patient session. A torso vest constructed according to the invention enables a catheterization session, including mapping and ablation to be performed without removing the vest from the subject.

In one aspect of the invention, the procedure is facilitated by use of a wearable vest containing different types of electrodes and sensors, which are required for position localization of the vest with respect to landmarks in the heart and elsewhere in the body.

Embodiments of the invention incorporate the different electrodes and elements into one wearable vest. The vest may use a number of different technologies, for example, printed circuits, printing on different materials with conductive ink, using different types of ink), and conductive wires sewn onto the fabric of the vest. The vest is connected, by wires or wirelessly, to a central controller such as that used in the CARTO® 3 System, available from Biosense Webster, Inc., 3333 Diamond Canyon Road, Diamond Bar, Calif. 91765.

In one aspect of the invention, the wearable vest is advantageously applied to mapping of intracardiac electropotentials. Typically this procedure requires insertion of a catheter with one or more electrodes into the heart, and tracking the catheter while acquiring the electropotentials. If the electropotentials change, for example, after an ablation procedure, the mapping must be repeated by another insertion of the catheter, and then re-mapping the heart.

In one phase of the inventive procedure, signals are emitted from an intracardiac catheter at a known location, and received as vest signals. Then, using the teachings of U.S. Patent Application Publication No. 2015/0133759 mutatis mutandis, a correspondence between receivers of the vest signals and the catheter location is determined. Once the correspondence has been generated, in a second phase of the procedure, it may be exploited for subsequent mapping of electropotentials in the heart at locations other than the catheter location without a further invasive procedure. For example, if the catheter location is in the left atrium, potentials the right atrium may also be mapped using the correspondence generated in the first phase. Additionally or alternatively a point in the left atrium that was never visited by the catheter can be mapped.

There is provided according to embodiments of the invention a method, which is carried out by clothing a subject in a torso vest that has a plurality of sensing electrodes, magnetic location sensors, active current location sensors and patches for establishing galvanic contact with the skin. The method is further carried out by placing the active current location sensors and the patches in galvanic contact with a body surface of the subject, inserting a multi-electrode probe into a chamber of a heart of the subject such that a plurality of intracardiac electrodes are disposed in a distal portion of the probe at respective locations in the heart. The method is further carried out by determining the respective locations using the active current location sensors, emitting electrical calibration signals from the intracardiac electrodes, receiving the calibration signals in the sensing electrodes of the torso vest, and determining relationships between the emitted calibration signals and the received calibration signals in the intracardiac electrodes to map a correspondence between the received calibration signals and the respective locations.

Another aspect of the method includes attaching a portion of the patches to electrocardiographic leads.

An additional aspect of the method includes returning ablation currents through at least one of the patches.

Another aspect of the method includes injecting cardiac pacing signals via at least one of the patches.

Yet another aspect of the method includes attaching body markers to the subject, and determining locations of the sensing electrodes with respect to the body markers.

According to one aspect of the method, determining locations of the sensing electrodes includes determining first locations of the body markers with respect to external fiducial markers, determining second locations of the magnetic location sensors of the torso vest with respect to the body markers, and computing the locations of the sensing electrodes with respect to the body markers from the second locations.

A further aspect of the method is carried out after removing the probe by clothing the subject in the torso vest a second time, and thereafter computing new locations of the sensing electrodes with respect to the body markers, adjusting the mapped correspondence to compensate differences between the locations of the sensing electrodes and the new locations of the sensing electrodes with respect to the body markers, rereading bioelectric signals from the respective locations in the heart with the sensing electrodes of the torso vest, and redetermining relationships between the reread bioelectric signals according to the adjusted mapped correspondence.

There is further provided according to embodiments of the invention an apparatus, including a torso vest, a plurality of sensing electrodes on the torso vest, a plurality of, magnetic location sensors on the torso vest, a plurality of active current location sensors on the torso vest, and a plurality of patches on the torso vest for establishing galvanic contact with the skin of a subject.

There is further provided according to embodiments of the invention an apparatus, including a probe adapted for insertion into a chamber of a heart of a living subject and having a plurality of intracardiac electrodes that can be disposed at respective locations in the heart, a torso vest having a plurality of sensing electrodes, magnetic location sensors, active current location sensors and patches for establishing galvanic contact with the skin, a first processor operative for determining the respective locations using the active current location sensors, a signal generator for delivering electrical calibration signals to the intracardiac electrodes for emission, and a second processor for receiving the calibration signals in the sensing electrodes of the torso vest and operative for determining relationships between the emitted calibration signals and the received calibration signals in the intracardiac electrodes to map a correspondence between the received calibration signals and the respective locations.

A further aspect of the apparatus includes a power generator for transmitting ablation currents that is connected to at least a portion of the intracardiac electrodes and to at least one of the patches for returning the ablation currents therethrough.

One aspect of the apparatus includes a pacing generator connected to at least one of the patches for injecting cardiac pacing signals therethrough.

BRIEF DESCRIPTION OF THE SEVERAL VIEWS OF THE DRAWINGS for a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a USB memory, hard drive, electronic media or CD-ROM. The code may be distributed on such media, or may be distributed to users from the memory or storage of one computer system over a network of some type to storage devices on other computer systems for use by users of such other systems.

A conventional method for mapping electropotentials of the heart, i.e., measuring intracardiac ECG signals, involves inserting a catheter with electrodes into the heart, and measuring potentials as the electrodes are moved to different locations within the heart.

Reverse ECG mapping attempts to generate an intracardiac ECG map by measuring body surface potentials at an array of positions on the skin of a patient. The method assumes that intracardiac ECG potentials $\vec{E}$ generate body surface potentials $\vec{S}$ S and that the two sets of potentials are related by an equation of the form:

$$\vec{S} = M \cdot \vec{E} \quad (1),$$

where M is a matrix, having elements $m_{ij}$.

U.S. Patent Application Publication No. 2015/0133759 takes an invasive approach to determine the matrix M. In an initial phase of a mapping procedure for a patient an electrode array, with electrodes in known positions, is attached to the patient's skin. Assuming the procedure is being performed, a system having location tracking capabilities is used. For example, the positions of the electrodes in the array and the electrodes of a cardiac catheter can be determined by the CARTO® 3 System, available from Biosense Webster, Inc., 3333 Diamond Canyon Road, Diamond Bar, Calif. 91765. Any other method for finding electrode position may be used.

The values of elements of the matrix M depend, inter alia, on the distance between the positions on the heart surface and the positions on the patient's skin, and on the conductivity of the material between these positions. U.S. Pat. No. 7,983,743 describes a non-invasive approach to estimate the matrix M (using systems such as MRI or CT to image the heart and thus find heart surface—skin distances). Vector $\vec{E}$ is then estimated from measured values of the vector $\vec{S}$.

System Overview.

Figure 1:
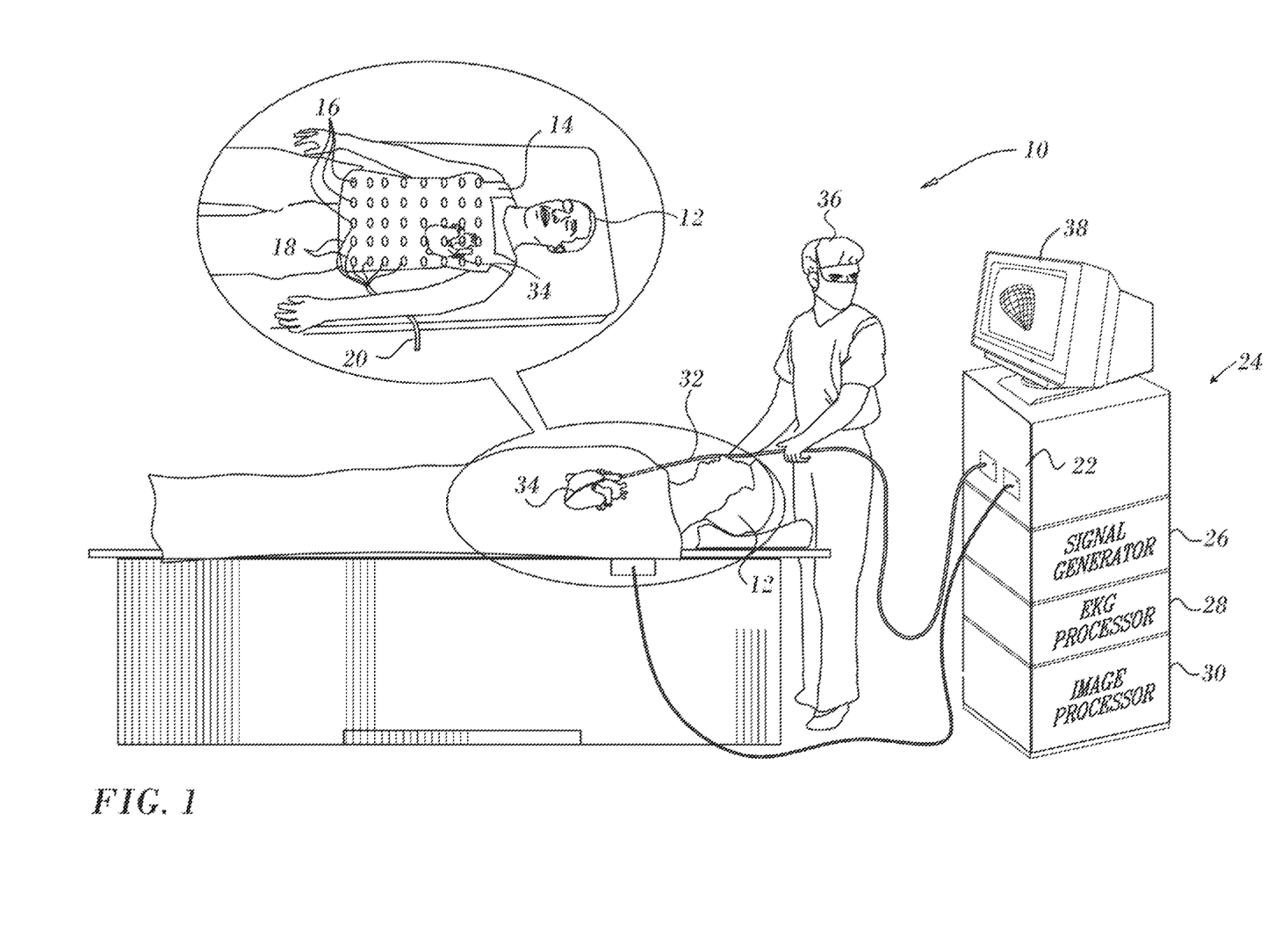
FIG. 1 is a pictorial illustration of a system, which is constructed and operative in accordance with an embodiment of the invention.

Reference is now made to FIG. 1, which is a pictorial illustration of a system 10, which is constructed and operative in accordance with an embodiment of the invention. A subject 12 is clothed in a torso vest 14. A plurality of sensing electrodes 16, typically between about 125 and 250 electrodes, are disposed within the torso vest 14 in galvanic contact with the skin of the subject 12, and can transmit and receive electrical potentials over the anterior, posterior and lateral aspects of the torso of the subject 12. The electrodes 16 are connected via leads 18 and cable 20 to a control and position processor 22, which is typically disposed in a console 24. The console 24 may include a signal generator 26, an EKG processor 28 and an image processor 30

A catheter 32 has been introduced into a heart 34 by an operator 36. Information relating to the data obtained from the catheter 32, the status of the electrodes 16 of the torso vest 14 and the signal generator 26, EKG processor 28 and image processor 30 may be displayed on a monitor 38.

Torso Vest.

Figure 2:
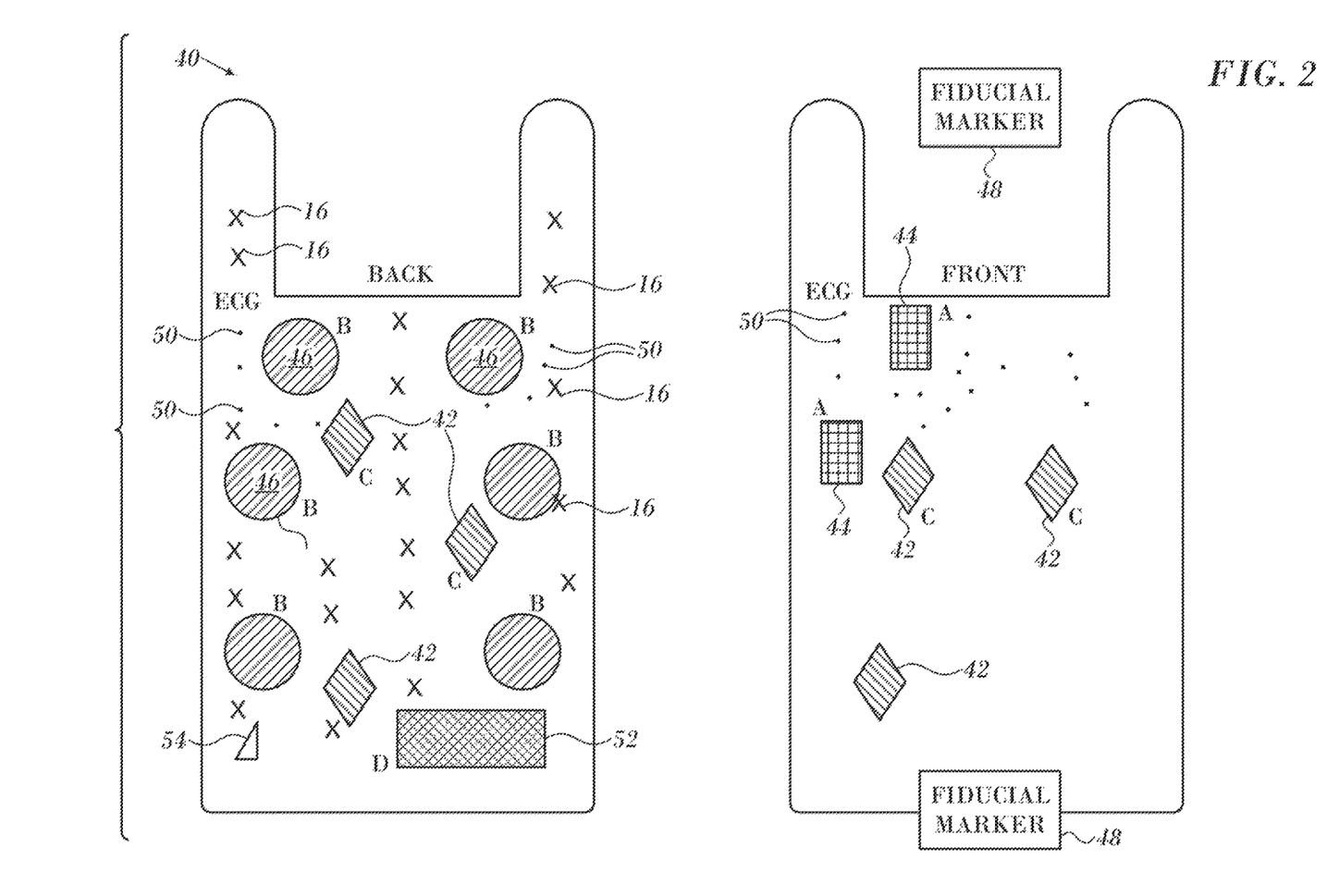
FIG. 2 shows front and back views of a wearable torso vest in accordance with an embodiment of the invention.

Reference is now made to FIG. 2, which are front and back views of a wearable torso vest 40 in accordance with an embodiment of the invention. In addition to the electrodes 16 shown in FIG. 1, several additional elements are incorporated in the vest 40 in many combinations, using different technologies: e.g., printed circuits, printing on different materials with conductive ink (also different types of ink), and conductive wires sewn onto fabric. The vest is connected, by wires or wirelessly, to a central controller such as that used in the Carto system.

The vest 40 may comprise active any number of current location sensors 42, which are in galvanic contact with the body of the patient when the vest is worn. In one embodiment there are six active current location sensors 42 arranged in three pairs. The position of a mapping catheter electrode in the heart can be derived from currents passing between the active current location sensors 42 and the electrode as taught in U.S. Patent Application Publication No. 2014/0221803 of Bar Tal et al., which is herein incorporated by reference.

The vest 40 may comprise defibrillation patches 44, and magnetic location sensors 46. The magnetic location sensors 46 enable the position of the vest to be determined with respect to fiducials 48 that are external to the vest 40 and the body of the patient. Such magnetic location sensors are described, for example, in U.S. Pat. Nos. 5,558,091, 5,443, 489, 5,480,422, 5,546,951, and 5,568,809, and International Publication Nos. WO 95/02995, WO 97/24983, and WO 98/29033, the disclosures of which are incorporated herein by reference.

The magnetic location sensors 46 may be used in conjunction with a modification of the techniques described in U.S. Patent Application Publication No. 2008/0294258, entitled Orthopaedic Monitoring System, Methods and Apparatus, which is herein incorporated by reference. Briefly, at least two markers that can be wirelessly tracked at radio frequencies are placed at convenient body landmarks. The landmarks could be the suprasternal notch and xiphoid process. The locations of the markers are determined with respect to external fiducials that are positioned in a working volume of a monitoring system of the markers, after which the position of the vest can be computed from information obtained from the magnetic location sensors 46 with respect to the fiducials, and hence with respect to locations in the heart that were determined by the active current location sensors.

The vest 40 may include skin patches 50 for standard ECG leads, and a skin patch 52 that can be incorporated in a circuit for return of ablation currents. Optionally, a skin patch 54 that can be included in a circuit for injecting cardiac pacing signals may be included. In the latter application the patch 54 can be used as a reference for unipolar pacing using device previously inserted in the body.

The console 24 (FIG. 1) contains electrical circuitry for impedance detection, as described in commonly assigned U.S. Pat. No. 9,370,312, whose disclosure is incorporated herein by reference. The system is modified to generate, based on impedance measurements between a small number of endocardial points and electrodes 56, a functional relationship therebetween. In one embodiment, this relationship is a linear multidimensional matrix of coefficients, referred to herein as a lead field matrix. The inverse of the matrix is then estimated, for example, as described in U.S. Patent Application Publication No. 2003/0120163 (Yoram Rudy et al.), whose disclosure is herein incorporated by reference. In this disclosure, the inverse matrix corresponds to epicardial electrical potentials. In the system 10, however, the inverse of the matrix may correspond to a map of endocardial conductances, which is an advance over prior techniques. In the past, it has not been possible to reliably evaluate the transfer function between external measurements and endocardial potentials. This is because the electrical field traverses fibromuscular tissue within the myocardium. As noted above, the amount and orientation of such tissue varies among individuals. Alternatively, in some embodiments of the system 10, the lead field matrix and its inverse may relate to a map based on epicardial conductances. Inversion of the lead field matrix is discussed in further detail below.

It is possible to use only one endocardial point. The receiving point or points can be internal or external to the subject. For example one or more esophageal leads coronary sinus electrodes, epicardial, or even intramyocardial electrodes can be used as receiving points.

Figure 3:
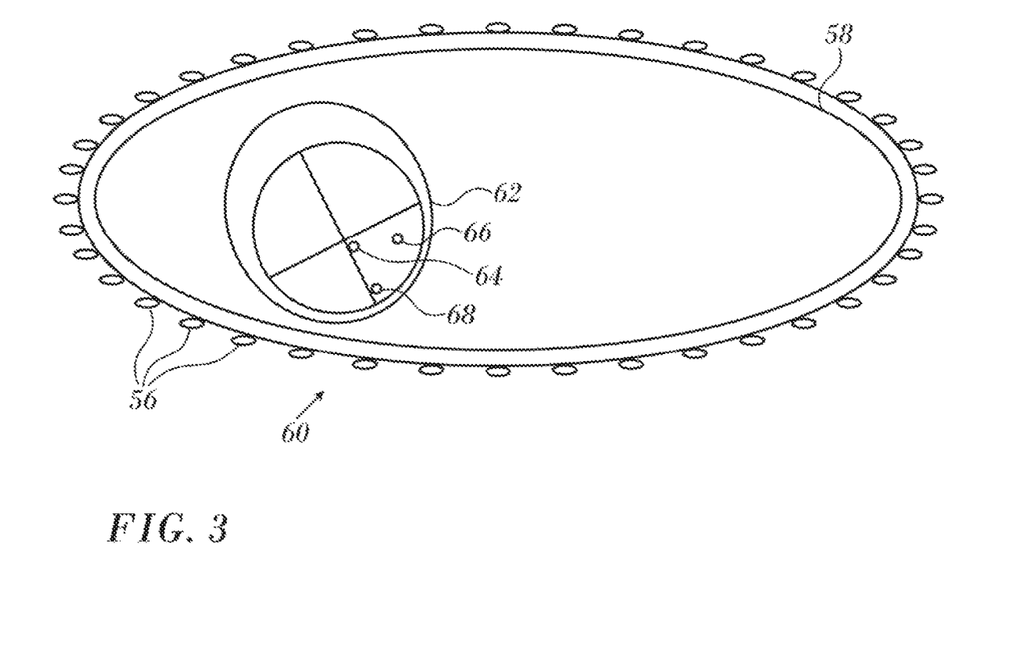
FIG. 3 is a simplified sectional view of a thorax in accordance with a disclosed embodiment of the invention.

Reference is now made to FIG. 3, which is a simplified sectional view of a thorax 58 showing a torso vest 60, and the electrodes 56 distributed about the thorax, in accordance with a disclosed embodiment of the invention. FIG. 3 also shows a right atrium 62, and includes three endocardial points 64, 66, 68. Impedance measurements may be made between catheter electrodes positioned at the endocardial points 64, 66, 68 and electrodes 56. In some applications, impedances are also measured between epicardially positioned electrodes (not shown in FIG. 3) and the electrodes 56.

Figure 4:
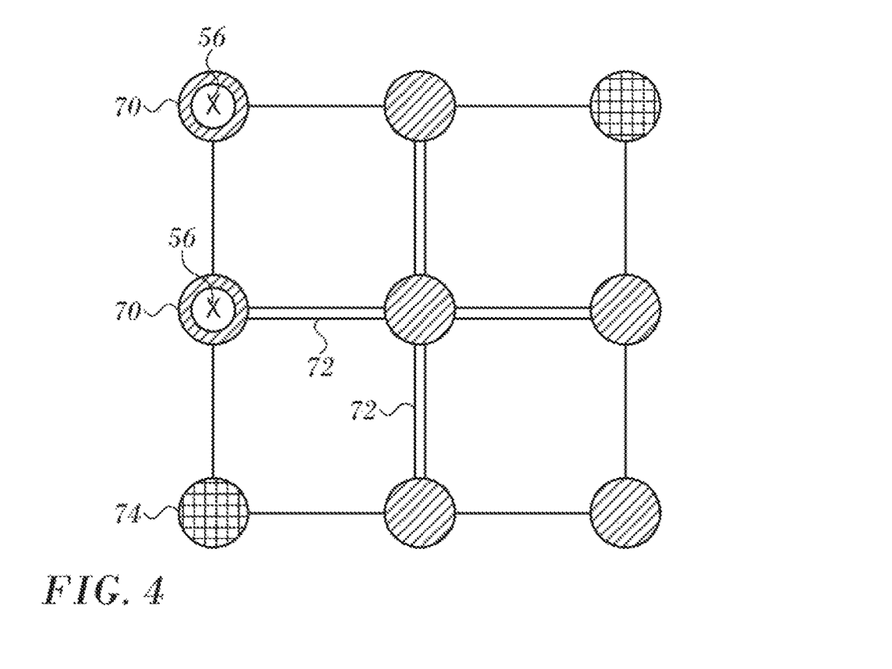
FIG. 4 is a schematic diagram illustrating details of a torso vest in accordance with a disclosed embodiment of the invention.

Reference is now made to FIG. 4, which is a schematic diagram illustrating details of the torso vest 60 (FIG. 3), in accordance with a disclosed embodiment of the invention. The torso vest 60 is constructed to include distributed stress points 70, which may coincide with the electrodes 56. However, such a coincidence is a matter of convenience, and is not essential. The stress points 70 are connected by flexible splines 72, having predetermined degrees of freedom. The splines 72 cause the torso vest 60 to closely conform to the geometry of the thorax 58 (FIG. 3). The torso vest 60 includes at least one location sensor 74, which is a reference point in a coordinate system that includes the electrodes 56. The use of such a location sensor is taught with reference to a locating system in commonly assigned U.S. Patent Application Publication No. 2004/0068178, whose disclosure is herein incorporated by reference. The location sensor 74 enables the positions of the electrodes 56 to be tracked during a medical procedure and to be related to intracardiac electrodes by difference computations. The location sensor 74 is not essential, so long as the electrodes 56 can be located relative to the endocardial points.

ACL and Ablation Circuitry.

Figure 5:
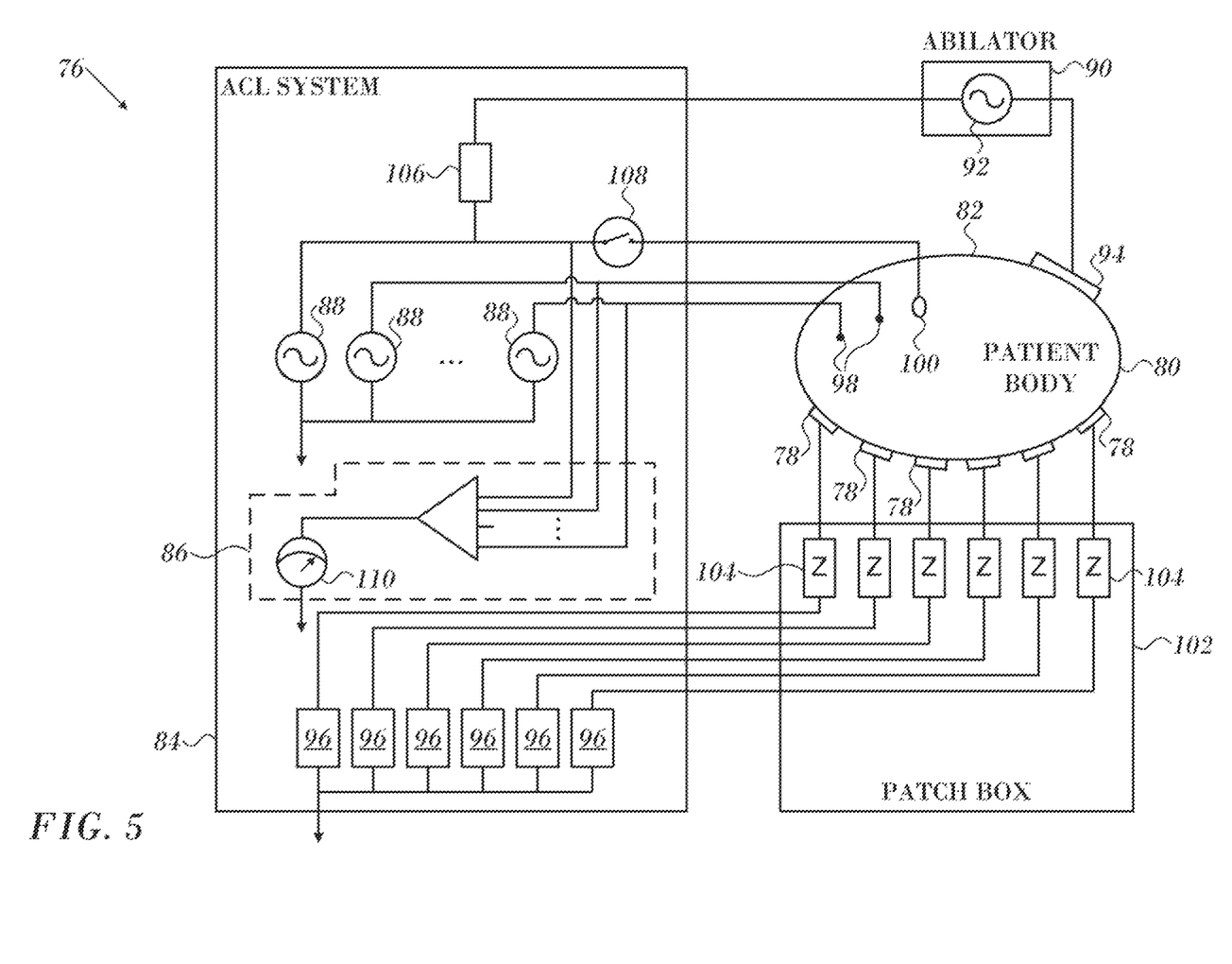
FIG. 5 is a schematic diagram of an ablation and active current location (ACL) circuit in accordance with an embodiment of the invention.

Reference is now made to FIG. 5, which is a schematic diagram of an ablation and active current location (ACL) circuit 76 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 78, which can be adhesive skin patches, are coupled to a body surface 80 (e.g., the skin) of subject 82. The body surface electrodes 78 are sometimes referred to herein as "patches". In cardiac applications the body surface electrodes 78 are usually distributed so as to surround the heart, three on the chest of the subject and three on the back. However, the number of the body surface electrodes 78 is not critical, and they may be placed at convenient locations on the body surface 80 in the general vicinity of the site of the medical procedure.

A control unit 84, normally disposed in the console 24 (FIG. 1), includes current measurement circuitry 86 and one or more catheter electrode transmitters 88 for driving a current through one or more of the electrodes 78 to one or more of the body surface electrodes 78 at respective working frequencies. The control unit 84 is linked to the positioning processor 22 (FIG. 1). The control unit 84 is linked to an ablator 90, which comprises at least one ablation generator 92. Currents through the body surface electrodes 78 and an ablator body surface electrode 94 flow in a circuit with the ablation generator 92 and are measured by respective current measurement circuits that are disposed within body electrode receivers 96, sometimes referred to herein as "patch measurement circuits". The body electrode receivers 96 are typically incorporated in the control unit 84. Alternatively, they may be affixed to the body surface electrodes 78. Catheter electrodes are represented in FIG. 5 as measurement electrodes 98 (circles) and a dual-purpose electrode 100 (ellipse). The dual-purpose electrode 100 functions as an ablation electrode and also serves as one of the measurement electrodes.

The body surface electrodes 78 are connected to the body electrode receivers 96 via a patch box 102, which protects the system from ablation and defibrillation currents. Typically the system is configured with six body electrode receivers 96. The patch box parasitic impedances 104 (Z), are measured during production and thus known a priori. These impedances are discussed below.

Typically, although only two measurement electrodes 98 are shown for convenience, about 80 measurement electrodes are used for impedance measurements. Typically there are one or two ablation electrodes. The coordinates of a catheter inside the body are determined in the positioning system in the console 24 (FIG. 1) by passing currents between electrodes on the catheter and the body surface electrodes 78.

The control unit 84 may also control an ablation circuit, comprising ablator 90, and the dual-purpose electrode 100. The ablator 90 is typically disposed externally to the control unit 84 and incorporates the ablation generator 92. It connects with the ablator body surface electrode 94 and to an ablator filter 106, which in this example is shown within the control unit 84. However this location is not essential. A switch 108 configures the ablator circuit for different modes of operation as described below. Voltage measurement circuitry 110 is provided for determining the output of the catheter electrode transmitters 88. It will be noted from inspection of FIG. 5 that the ablation circuit is connected to one of the catheter electrode transmitters 88.

Body Markers

Figure 6:
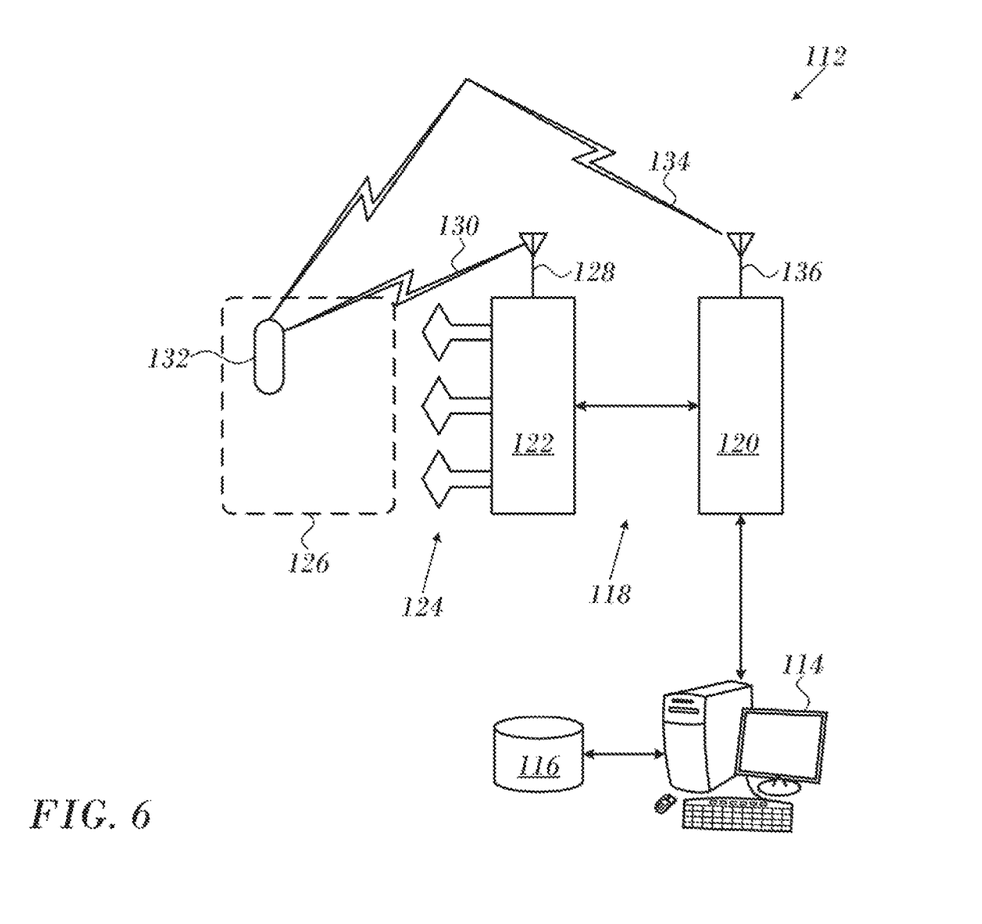
FIG. 6 is a schematic block diagram of a body marker monitoring system in accordance with an embodiment of the invention.

Reference is now made to FIG. 6, which is a schematic block diagram of a body marker monitoring system 112 in accordance with an embodiment of the invention. The monitoring system includes wireless tracking functionality as well as assessment functionality. The assessment functionality is generally implemented by a computer 114 carrying out various data processing operations on positional data items, and other data items, stored in database or databases 116. The positional data items are obtained by wirelessly tracking markers. A wireless tracking sub-system 118 is provided by computer 114, positional signal processing circuitry 120 and monitoring or tracking station comprising sub-system 122.

Sub-system 122 includes three magnetic field generator coils 124. The three coils generate a magnetic field 126, which extends over a working volume of the monitoring system. The monitoring system also includes an antenna 128, which wirelessly transmits an electrical power signal 130 at an RF frequency to a marker 132 located within the working volume. Marker 132 wirelessly transmits signals 134 in which are digitally encoded the position and orientation of the marker and also a unique identifier for the marker. The signals 134 are received by an antenna 136 in communication with the positional signal processing circuitry 120.

A suitable marker 132 and associated tracking sub-system 118 for use in the monitoring system 112 will briefly be described in greater detail. Aspects of the marker 132 and tracking sub-system 118 are described in greater detail in U.S. Patent Publication no. US 2003/0120150 A1 (U.S. patent application Ser. No. 10/029,473), which is incorporated herein by reference in its entirety for all purposes.

The marker, or wireless position sensor, 132, which can be tracked by the tracking sub-system 112, has a housing for the marker. As explained above, the marker 132 generates and wirelessly transmits digital signals 134 encoding data items indicative of the marker's location (x, y and z coordinates within the Cartesian reference frame of the tracking system) and orientation (pitch, roll and yaw), in response to the external magnetic field 126 produced by the three magnetic field generator coils 124 (also referred to as radiator coils).

Circuitry is present in the monitoring system and further circuitry is present in positional signal processing circuitry. The magnetic field generator coils 124 are driven by driver circuits to generate electromagnetic fields at different, respective sets of frequencies. The sets of frequencies at which the coils radiate are set by computer 114, which serves as the system controller for tracking sub-system 118. The respective sets of frequencies may all include the same frequencies, or they may include different frequencies. In any case, computer 114 controls driver circuits according to a known multiplexing pattern, which provides that at any point in time, no more than one field generator coil is radiating at any given frequency. Typically, each driver circuit is controlled to scan cyclically over time through the frequencies in its respective set. Alternatively, each driver circuit may drive a respective one of magnetic field generator coils 124 to radiate at multiple frequencies simultaneously.

For the purposes of system sub-system 122, magnetic field generator coils 124 may be arranged in any convenient position and orientation, so long as they are fixed in respect to some reference frame, and so long as they are non-overlapping, that is, there are no two field generator coils with the exact, identical location and orientation. Typically, for surgical applications the coils are located in a triangular arrangement. The coil axes may be parallel, or they may alternatively be inclined. Bar-shaped transmitters or even triangular or square-shaped coils could also be useful for such applications.

In surgical applications, it is desirable that magnetic field generator coils 124 be positioned away from the surgical field, so as not to interfere with the surgeon's freedom of movement. On the other hand, the coils should be positioned so that the working volume 126 of the tracking system includes the entire area in which the surgeon is operating. At the same time, the locations and orientations of magnetic field generator coils 124 should be known relative to a given reference frame in order to permit the coordinates of marker 132 to be determined in that reference frame. In practice, magnetic field generator coils 124 are mounted on a reference structure part of the sub-system 122.

The marker 132 include sensor coils, in which electrical currents are induced to flow in response to the magnetic fields produced by magnetic field generator coils 124. The sensor coils may be wound on either air cores or cores of magnetic material. Typically, each marker comprises three sensor coils, having mutually orthogonal axes, one of which is conveniently aligned with a principal axis of the housing, such as a longitudinal axis. The three coils may be concentrically wound on a single core, or alternatively, the coils may be non-concentrically wound on separate cores, and spaced along the principal axis. The use of non-concentric coils is described, for example, in the PCT Patent Publication WO 96/5968 and in the corresponding U.S. patent application Ser. No. 09/414,875, which are incorporated herein by reference in their entirety for all purposes.

Alternatively, the marker 132 may each comprise only a single sensor coil or two sensor coils. Further alternatively, marker 132 may comprise magnetic position sensors based on sensing elements of other types known in the art, such as Hall effect sensors.

At any instant in time, the currents induced in the sensor coils comprise components at the specific frequencies generated by magnetic field generator coils 124. The respective amplitudes of these currents (or alternatively, of time-varying voltages that may be measured across the sensor coils) are dependent on the location and orientation of the marker relative to the locations and orientations of the field generator coils. In response to the induced currents or voltages, signal processing and transmitter circuitry in each marker generate and transmit signals 134 that are indicative of the location and orientation of the sensor. These signals are received by receiving antenna 136, which is coupled to computer 114 via signal receiver and demodulation circuitry. The computer processes the received signals, together with a representation of the signals used to drive the field generator coils, in order to calculate location and orientation coordinates of the implantable marker. The coordinates are processed and stored by the computer 114 as will be described in greater detail below.

When a metal or other magnetically-responsive article is brought into the vicinity of an object being tracked, the magnetic fields in this vicinity are distorted. There can be a substantial amount of conductive and permeable material in a surgical environment, including basic and ancillary equipment (operating tables, carts, movable lamps, etc.), as well as invasive surgery apparatus (scalpels, scissors, etc.). The magnetic fields produced by magnetic field generator coils 124 may generate eddy currents in such articles, and the eddy currents then cause a parasitic magnetic field to be radiated. Such parasitic fields and other types of distortion can lead to errors in determining the position of the object being tracked.

In order to alleviate this problem, the elements of the sub-system 118 and other articles used in the vicinity of the monitoring system are typically made of non-metallic materials when possible, or of metallic materials with low permeability and conductivity. In addition, computer 114 may be programmed to detect and compensate for the effects of metal objects in the vicinity of the monitoring system. Exemplary methods for such detection and compensation are described in U.S. Pat. Nos. 6,147,480 and 6,373,240, as well as in U.S. patent application Ser. No. 10/448,289, filed May 29, 2003 and Ser. No. 10/632,217 filed Jul. 31, 2003, incorporated herein by reference.

The marker in this embodiment comprises three sets of coils: sensor coils, power coils, and a communication coil. Alternatively, the functions of the power and communication coils may be combined, as described in U.S. patent application Ser. No. 10/029,473. The coils are coupled to electronic processing circuitry, which is mounted on a suitable substrate, such as a flexible printed circuit board (PCB). Details of the construction and operation of the circuitry are described in U.S. patent application Ser. No. 10/029,473 and in U.S. patent application Ser. No. 10/706,298, which are incorporated herein by reference in their entirety for all purposes.

Marker 132 can include only a single sensor coil and a single power coil, but in practice marker 132 typically comprises multiple coils of each type, such as three sensor coils and three power coils. The sensor coils are wound together, in mutually-orthogonal directions, on a sensor core, while the power coils are wound together, in mutually-orthogonal directions, on a power core. Alternatively, the sensor and power coils may be overlapped on the same core, as described, for example in U.S. Pat. No. 6,995,729 to Govari, whose disclosure is incorporated herein by reference. It is generally desirable to separate the coils one from another by means of a dielectric layer (or by interleaving the power and sensor coils when a common core is used for both) in order to reduce parasitic capacitance between the coils.

In operation, power coils serve as a power source for marker 132. The power coils receive energy by inductive coupling from external driving antenna 128 attached to RF power driving circuitry. Typically, the driving antenna radiates an intense electromagnetic field at a relatively high radio frequency (RF), such as in the range of 13.5 MHz. The driving field causes currents to flow in power coils, which are rectified in order to power the circuitry. Meanwhile, field generator coils 124 induce time-varying signal voltages to develop across the sensor coils as described above. The circuitry senses the signal voltages, and generates output signals in response thereto. The output signals may be either analog or digital in form. The circuitry drives the communication coil to transmit the output signals to receiving antenna 136 outside the patient's body. Typically, the output signals are transmitted at still higher radio frequencies, such as frequencies in the rage of 43 MHz or 915 MHz, using a frequency-modulation scheme, for example. Additionally or alternatively, the coil may be used to receive control signals, such as a clock signal, from a transmitting antenna (not shown) outside the patient's body.

As explained above, the driver circuitry also comprises an RF power driver, which drives antenna 128 to emit power signal 130, preferably in the 2-10 MHz range. The power signal causes a current to flow in power coil, which is rectified by circuitry and used to power the markers internal circuits. Meanwhile, the electromagnetic fields produced by magnetic field generator coils 124 cause currents to flow in the sensor coil. This current has frequency components at the same frequencies as the driving currents flowing through the magnetic field generator coils 124. The current components are proportional to the strengths of the components of the respective magnetic fields produced by the generator coils in a direction parallel to the sensor coil axes. Thus, the amplitudes of the currents indicate the position and orientation of the sensor coils relative to fixed magnetic field generator coils 124.

The circuitry measures the currents flowing in the sensor coils at the different field frequencies. It encodes this measurement in a high-frequency signal, which it then transmits back via an antenna to antenna 136. The circuitry comprises a sampling circuit and analog/digital (A/D) converter, which digitizes the amplitude of the current flowing in the sensor coils. In this case, the circuitry generates a digitally-modulated signal, and RF-modulates the signal for transmission by the antenna. Any suitable method of digital encoding and modulation may be used for this purpose. The circuitry also stores a unique identifier for each marker and similarly generates a digitally-modulated signal, and RF-modulates the signals 134 for transmission by the antenna. Other methods of signal processing and modulation will be apparent to those skilled in the art.

The digitally-modulated signal transmitted by the antenna is picked up by a receiver, coupled to antenna 136. The receiver demodulates the signal to generate a suitable input to signal processing circuits, which can be separate to, or integrated in, the computer 114. Typically, the receiver amplifies, filters and digitizes the signals from marker 132. The digitized signals are received and used by the computer 114 to compute the position and orientation of marker 132. General-purpose computer 114 is programmed and equipped with appropriate input circuitry for processing the signals from the receiver.

Preferably, the receiver circuitry includes a clock synchronization circuit, which is used to synchronize the driver circuits and RF power driver. The RF power driver can operate at a frequency that is an integer multiple of the driving frequencies of field magnetic field generator coils 124. The marker circuitry can then use the RF signal received by the power coil not only as its power source, but also as a frequency reference. Using this reference, marker circuitry is able to apply phase-sensitive processing to the current signals generated by the sensor coils, to detect the sensor coil currents in phase with the driving fields generated by magnetic field generator coils 124. The receiver can apply phase-sensitive processing methods, as are known in the art, in a similar manner, using the input from the clock synchronization circuit. Such phase-sensitive detection methods enable marker 132 to achieve an enhanced signal/noise (S/N) ratio, despite the low amplitude of the current signals in the sensor coils.

Although certain frequency ranges are cited above by way of example, those skilled in the art will appreciate that other frequency ranges may be used for the same purposes.

Marker circuitry also stores a unique identifier for marker 132 and the unique identifier is also transmitted to the tracking sub-system 118, so that the tracking sub-system can determine the identity of the marker from which positional data is being received. Hence the tracking sub-system can discriminate between different markers when multiple markers are present in the working volume 126 of the monitoring system.

An advantage of using wireless markers, such as marker 132, without an on-board power source, is that the markers can be inserted in and then left inside the patient's body for later reference.

Operation.

The apparatus described above is utilized to establish a mapping correspondence between electrical signals originating at respective locations in the heart and readings from an array of electrodes on a multi-electrode chest panel for acquisition of electrophysiologic data, and as a component of an ablation circuit. The procedure is facilitated by use of the combination vest 40 (FIG. 2). An entire session can be accomplished without removing the combination vest 40 from the subject.

Figure 7:
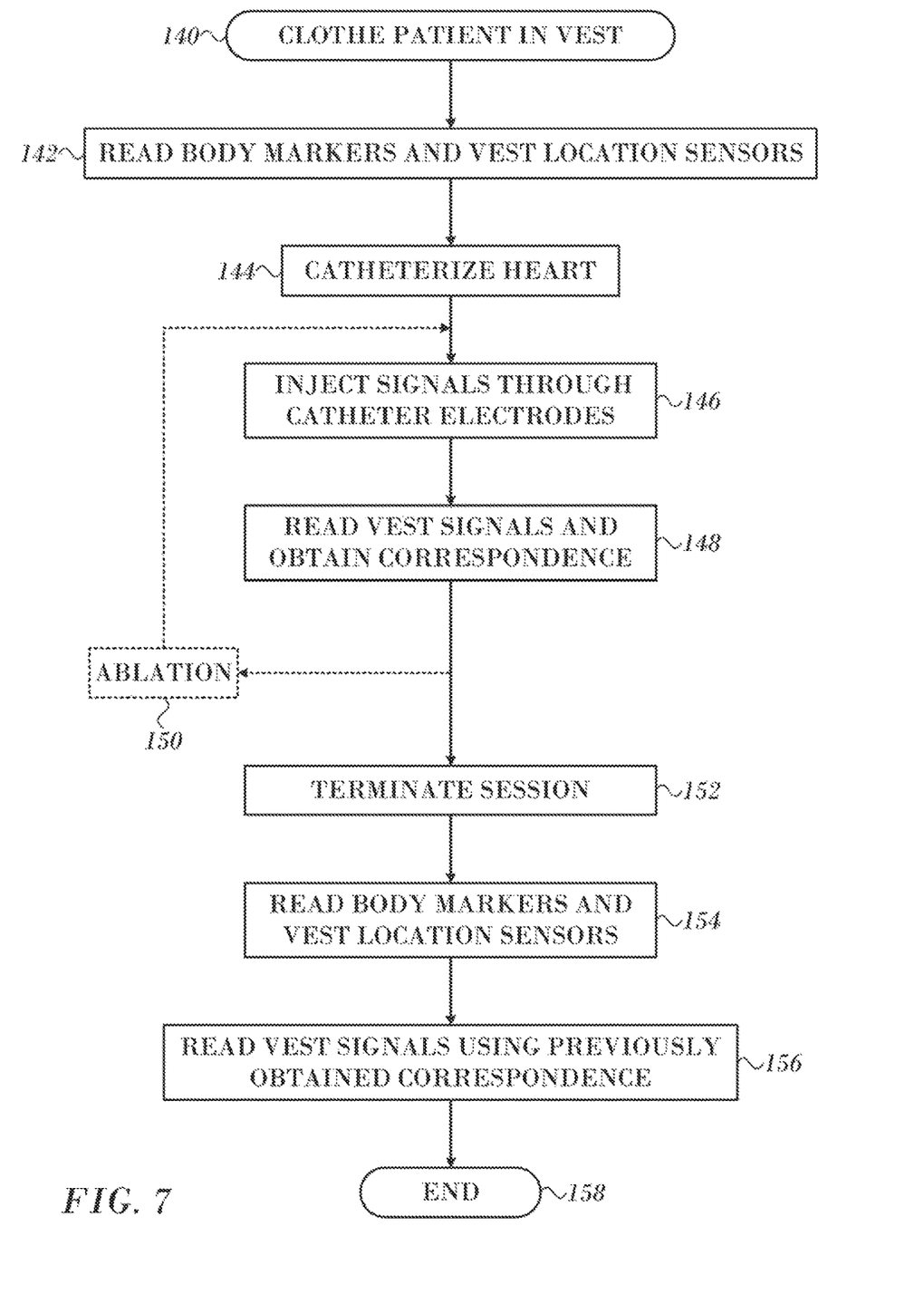
FIG. 7 is a flow chart of a method of correlating cardiac electrical maps with body surface measurements, in accordance with an embodiment of the invention.

Reference is now made to FIG. 7, which is a flow chart of a method of correlating cardiac electrical maps with body surface measurements, in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

A first phase of the method begins in a preparatory initial step 140. If not already implanted, body markers are placed on the skin, e.g., at the suprasternal notch and xiphoid process. The patient is clothed in vest 40 and the electrodes, leads, and skin patches attached to respective components of the console 24, such as the signal generator 26 and EKG processor 28. Initial step 140 can be executed quickly, relative to procedures where the vest 40 is not available. This minimizes discomfort for the patient, and increases the efficiency of usage of the catheterization facility.

Next, at step 142 readings are taken to establish the location of the body markers with respect to external fiducial markers, and the location of the magnetic location sensors 46 with respect to the body markers. This procedure accurately relates structures on the vest 40 to the patient's body, including internal locations in the heart at constant phases in the cardiorespiratory cycle.

Next, at step 144 the heart is catheterized conventionally, using a multielectrode mapping catheter. Then in step 146 Using the methods of the above noted U.S. Patent Application Publication Nos. 2008/0058657 and 2015/0133759, mutatis mutandis, signals from a signal generator are injected through the electrodes of the mapping catheter. At step 148 the injected signals are read in the array of electrodes in the vest 40. This step enables a correspondence between the mapped locations in the heart and the vest signals to be computed. By navigating the catheter in the heart many areas may be mapped with a desired spatial resolution. Indeed, the resolution can be effectively enhanced by using interpolation methods as taught in commonly assigned application Ser. No. 15/351,972, entitled Marking Sparse Areas on Maps, which is herein incorporated by reference. Unmapped chambers can be evaluated by using a pre-acquired image registered to a mapped chamber that also includes the unmapped chamber. Appropriate ECG signals can be superimposed on the mapping if desired.

Optionally, at step 150 ablation may be carried out on a target of interest. The lesion produced is intended to affect the time-varying electrical potentials in other areas of the heart, as is known, for example, from U.S. Pat. No. 6,997,924 to Schwartz et al., which is herein incorporated by reference. After performing step 150 control returns to step 146 so that the effect of the ablation on the vest signals can be reevaluated in step 148. When ablation is completed or not performed the session is terminated at step 152. The steps up to this point can be performed without removing the vest 40. It can be removed in step 152.

Subsequently in a new session, the bioelectric signals generated in the heart can be evaluated non-invasively. At step 154 the patient is re-clothed in the vest 40 and readings of the body markers and location sensors on the vest obtained as described above in step 152. The correspondence between the mapped locations in the heart and the vest signals is recomputed or adjusted for differences between the locations of the sensing electrodes 16 and the respective locations in the heart due to repositioning the vest 40. Then, at step 156, electrical signals are read from the array of electrodes on the vest, their sources located using the adjustment of the correspondence obtained in step 148, and intracardiac potentials calculated at the respective sources.

Thereafter, the vest may be removed and the session terminated in final step 158.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   clothing a subject in a torso vest having a plurality of sensing electrodes, magnetic location sensors, active current location sensors and patches for establishing galvanic contact with skin of the subject;
   without removing the torso vest from the subject, performing the steps of:
   placing the active current location sensors and the patches in galvanic contact with a body surface of the subject;
   inserting a probe into a chamber of a heart of the subject, a plurality of intracardiac electrodes being disposed at respective locations in the heart;
   determining the respective locations using the active current location sensors;
   emitting electrical calibration signals from the intracardiac electrodes;
   receiving the calibration signals in the sensing electrodes of the torso vest; and
   determining relationships between the emitted calibration signals and the received calibration signals in the intracardiac electrodes to map a correspondence between the received calibration signals and the respective locations.

2. The method according to claim 1, further comprising attaching a portion of the patches to electrocardiographic leads.

3. The method according to claim 1, further comprising returning ablation currents through at least one of the patches.

4. The method according to claim 1, further comprising injecting cardiac pacing signals via at least one of the patches.

5. The method according to claim 1, further comprising the steps of:
   attaching body markers to the subject; and
   determining locations of the sensing electrodes with respect to the body markers.

6. The method according to claim 5, wherein determining locations of the sensing electrodes comprises:
   determining first locations of the body markers with respect to external fiducial markers;
   determining second locations of the magnetic location sensors of the torso vest with respect to the body markers; and
   computing the locations of the sensing electrodes with respect to the body markers from the second locations.

7. The method according to claim 5, further comprising the steps of:
- after removing the probe clothing the subject in the torso vest a second time;
- thereafter computing new locations of the sensing electrodes with respect to the body markers;
- adjusting the mapped correspondence to compensate differences between the locations of the sensing electrodes and the new locations of the sensing electrodes with respect to the body markers;
- rereading bioelectric signals from the respective locations in the heart with the sensing electrodes of the torso vest; and
- redetermining relationships between the reread bioelectric signals according to the adjusted mapped correspondence.

8. An apparatus, comprising:
- a probe adapted for insertion into a chamber of a heart of a living subject and having a plurality of intracardiac electrodes that can be disposed at respective locations in the heart;
- a torso vest having a plurality of sensing electrodes, magnetic location sensors, active current location sensors and patches for establishing galvanic contact with the skin;
- a first processor operative for determining the respective locations using the active current location sensors;
- a signal generator delivering electrical calibration signals to the intracardiac electrodes for emission; and
- a second processor receiving the calibration signals in the sensing electrodes of the torso vest and operative for determining relationships between the emitted calibration signals and the received calibration signals in the intracardiac electrodes to map a correspondence between the received calibration signals and the respective locations.

9. The apparatus according to claim 8, further comprising a power generator for transmitting ablation currents connected to at least a portion of the intracardiac electrodes and to at least one of the patches for returning the ablation currents therethrough.

10. The apparatus according to claim 8, further comprising a pacing generator connected to at least one of the patches for injecting cardiac pacing signals therethrough.

11. The apparatus according to claim 8, further comprising a body marker attachable to the subject and wireless tracking circuitry for determining a location of the body marker with respect to the torso vest.

\* \* \* \* \*